(12) United States Patent
Kim et al.

(10) Patent No.: US 10,039,825 B2
(45) Date of Patent: *Aug. 7, 2018

(54) COMBINATION THERAPY WITH CD4 LYMPHOCYTE DEPLETION AND MTOR INHIBITORS

(71) Applicant: Cedars-Sinai Medical Center, Los Angeles, CA (US)

(72) Inventors: Hyung Kim, Los Angeles, CA (US); Yanping Wang, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/218,464

(22) Filed: Jul. 25, 2016

(65) Prior Publication Data

US 2017/0021016 A1 Jan. 26, 2017

Related U.S. Application Data

(63) Continuation of application No. 14/537,753, filed on Nov. 10, 2014, now Pat. No. 9,427,463, which is a continuation of application No. 13/641,434, filed as application No. PCT/US2011/033191 on Apr. 20, 2011, now Pat. No. 8,906,374.

(60) Provisional application No. 61/326,095, filed on Apr. 20, 2010.

(51) Int. Cl.
*A61K 39/395* (2006.01)
*A61K 31/436* (2006.01)
*A61K 45/06* (2006.01)
*C07K 16/28* (2006.01)
*A61K 39/00* (2006.01)

(52) U.S. Cl.
CPC ........ *A61K 39/3955* (2013.01); *A61K 31/436* (2013.01); *A61K 45/06* (2013.01); *C07K 16/2812* (2013.01); *A61K 2039/505* (2013.01); *C07K 2317/24* (2013.01)

(58) Field of Classification Search
CPC .......... C07K 16/2812; A61L 2039/505; A61K 39/395–39/39558; A61K 2039/505
See application file for complete search history.

(56) References Cited

U.S. PATENT DOCUMENTS

| | | | |
|---|---|---|---|
| 8,906,374 B2 | 12/2014 | Kim et al. | |
| 9,427,463 B2 * | 8/2016 | Kim | A61K 31/436 |
| 2006/0051357 A1 | 3/2006 | Katopodis et al. | |
| 2008/0031882 A1 | 2/2008 | Liang et al. | |
| 2008/0112888 A1 | 5/2008 | Wang | |
| 2009/0226430 A1 | 9/2009 | Hanna et al. | |
| 2009/0311249 A1 | 12/2009 | Gianni et al. | |
| 2010/0055102 A1 | 3/2010 | Langermann | |
| 2010/0196311 A1 | 8/2010 | Kim et al. | |
| 2013/0028898 A1 | 1/2013 | Kim et al. | |
| 2015/0064180 A1 | 3/2015 | Kim et al. | |
| 2017/0007698 A1 * | 1/2017 | Kim | A61K 39/0011 |

FOREIGN PATENT DOCUMENTS

| | | |
|---|---|---|
| CA | 2937035 A1 | 8/2015 |
| CN | 105979961 A1 | 9/2016 |
| EP | 3102233 A1 | 12/2016 |
| IN | 201617026443 A | 8/2016 |
| JP | 2017507931 A1 | 3/2017 |
| WO | 199701002 A1 | 3/1997 |
| WO | WO 2004045512 | 6/2004 |
| WO | 2006050172 A2 | 5/2006 |
| WO | WO 2007130555 | 2/2007 |
| WO | 2010124498 A1 | 3/2010 |
| WO | WO 2011133636 | 10/2011 |
| WO | 2013/043647 A1 | 3/2013 |
| WO | 2015120198 A1 | 8/2015 |

OTHER PUBLICATIONS

ISR for PCT/US2011/33191 dated Jun. 29, 2011.
IPRP for PCT/US2011/33191 dated Oct. 23, 2012.
Written Opinion for PCT/US2011/33191 dated Jun. 18, 2011.
Marzec et al. IL-2-and IL-15-induced activation of the rapamycin-sensitive mTORC1 pathway in malignatnt CD4+ T lymphocytes. Blood (2008).111:2181-89.
Rider et al. A Human CD4 Monoclonal Antibody for the Treatment of T-Cell Lymphoma Combines Inhibition of T-Cell Signaling by a Dual Mechanism with Potent Fc-Dependent Effector Activity. Cancer Res. (2007). 67(2):9945-53.
Kataja et al. Primary breast cancer: ESMO Clinical Recommendations for diagnosis, treatment and follow-up. Ann Oncol (2009). 20(Supplemental 4): iv 10-14.
Balmana et al. BRCA in breast cancer: ESMO Clinical Recommendations. Ann Oncol (2009). 20(Supplemental 4): iv 19-20.
Nelson et al. Screening for Breast Cancer: An Update for the U.S. Preventive Services Task Force. Ann Intern Med (2009).151:727-737.

(Continued)

*Primary Examiner* — Jessica H Roark
(74) *Attorney, Agent, or Firm* — Suwei Zhu; Nixon Peabody LLP

(57) ABSTRACT

The invention provides methods for treating a malignant neoplastic cell proliferative disorder or disease, comprising administering to a subject in need thereof an effective amount of an mTOR inhibitor and an effective amount of a CD4 lymphocyte depleting agent. Such methods find utility in the treatment of certain subsets of malignant neoplastic cell proliferative disorders or diseases, e.g. renal cell carcinoma and melanoma. The invention also provides for pharmaceutical compositions comprising a therapeutically effective amount of an mTOR inhibitor and an effective amount of a CD4 lymphocyte depleting agent in a pharmaceutically acceptable carrier.

13 Claims, 6 Drawing Sheets

(56) References Cited

OTHER PUBLICATIONS

Li et al. CD8+ T-Cell Depletion and Rapamycin Synergize with Combined Coreceptor/Stimulation Blockade to Induce Robust Limb Allograft Tolerance in Mice. Am J Transplant (2008). 8:2527-2536.

Restifo et al. Adoptive immunotherapy for cancer: harnessing the T cell response. Nature Reviews (2012). 12:269-281.

Saroj et al. An overview on Immunomodulation. Journal of Advanced Scientific Research (2012). 3(1):7-12.

Toka et al. CD4+ CD25+ T Cells Regulate Vaccine-Generated Primary and Memory CD8+ T-Cell Responses against Herpes Simplex Virus Type 1. J Virol (2004). 78(23):13082-13089.

Morse et al. Depletion of human regulatory T cells specifically enhances antigen-specific immune responses to cancer vaccines. Blood (2008). 112:610-618.

Jing et al. Depletion of CD4 T cells enhances immunotherapy for neuroblastoma after syngeneic HSCT but compromises development of antitumor immune memory. Blood (2009). 113(18):4449-4457.

Radvanyi et al. Antagonist Antibodies to PD-1 and B7-H1 (PD-L1) in the Treatment of Advanced Human Cancer—Letter. Clin Cancer Res (2013). 19(19): 2 pages.

Goding et al. Restoring immune function of tumor-specific CD4+ T cells during recurrence of melanoma. J Immunol (2013). 090(9):4899-4909.

PCT/US2015/014687 International Search Report and Written Opinion dated Apr. 21, 2015; 8 pages.

Partial Search Report for EP15747022.0 dated Aug. 7, 2017, 15 pages.

Arora et al., Effect of CD4-Depleting Antibody on the Development of Cryptococcus Neoformans-Induced Allergic Bronchopulmonary Mycosis in Mice, Infection and Immunity, 2006, vol. 74(7), pp. 4339-4348.

Kim et al., Clinical Efficacy of Zanolimumab (HuMax-CD4): Two Phase 2 Studies in Refractory Cutaneous T-Cell Lymphoma, Blood, 2007, vol. 109(11), pp. 4655-4622.

PCT/US2015/014687 International Preliminary Report on Patentability dated Aug. 9, 2016; 7 pages.

European Search Report for EP15747022.0 dated Oct. 25, 2017, 24 pages.

Madeleine Duvic, Systemic Monotherapy vs. Combination Therapy for CTCL: Rationale and Future Strategies, Cancer Network, Oncology Journal, 2007, vol. 21, 5 pages.

* cited by examiner

Control      CD4 lymphocyte depletion and mTOR inhibitor

COMBINATION THERAPY WITH CD4 LYMPHOCYTE DEPLETION AND MTOR INHIBITORS

CROSS-REFERENCE TO RELATED APPLICATIONS

This application claims the benefit of priority under 35 U.S.C. § 120 as a continuation of U.S. patent application Ser. No. 14/537,753 filed Nov. 10, 2014, and issued as U.S. Pat. No. 9,427,463 on Aug. 30, 2016, which is a continuation of U.S. patent application Ser. No. 13/641,434 filed Oct. 15, 2012, and issued as U.S. Pat. No. 8,906,374 on Dec. 9, 2014, which is the National Phase of International Application No. PCT/US2011/033191 filed Apr. 20, 2011, now expired, which designated the U.S. and that International Application was published under PCT Article 21(2) in English, which claims priority under 35 U.S.C. § 119(e) to U.S. patent application serial No. 61/326,095 filed Apr. 20, 2010, now expired, the contents of each of which are herein incorporated by reference.

STATEMENT REGARDING FEDERALLY SPONSORED RESEARCH OR DEVELOPMENT

This invention was made with government support under Grant No. CA120075 awarded by the National Institutes of Health. The government has certain rights in the invention.

FIELD OF THE INVENTION

The invention relates to methods for treating malignant neoplastic cell proliferative disorders with mTOR inhibitors and CD4 lymphocyte depleting agents.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cancer vaccines have the potential to target tumors while sparing normal tissue. There is also renewed interest in immunotherapies for malignancies; the FDA recently approved Provenge®, which will be the first commercially available cancer vaccine for the treatment of a solid tumor (15). It is surprising that Provenge® has been approved for advanced prostate cancer, which is not considered a classic immunoresponsive disease. This suggests that cancer vaccines may be effective for many malignancies, and it is expected that important lesson learned while developing Provenge® will facilitate the development of vaccines for other malignancies.

The mammalian target of rapamycin, mTOR (also known as mechanistic target of rapamycin and FK506 binding protein 12-rapamycin associated protein 1 (FRAP1)), is a protein which in humans is encoded by the FRAP1 gene (1, 2). mTOR is a serine/threonine protein kinase involved in the regulation of protein synthesis, transcription, cell growth, cell proliferation, cell motility, and cell survival (3, 4). mTOR is a pivotal regulator of cell proliferation. mTOR integrates the input from upstream pathways, including mitogens, insulin, and growth factors (such as IGF-1 and IGF-2) (3). In addition, mTOR senses cellular nutrient and energy levels and cellular redox status (5). The mTOR pathway is dysregulated in many human diseases, especially certain cancers (4).

The immunosuppressive effects of mTOR inhibition are well known; mTOR inhibition with rapamycin or one of the rapamycin analogs is part of the standard regimen for immune suppression following organ transplantation. Rapamycin, the prototypic mTOR inhibitor, is a bacterial product that can inhibit mTOR by associating with its intracellular receptor FKBP12 (6, 7). The FKBP12-rapamycin complex binds directly to the FKBP12-Rapamycin Binding (FRB) domain of mTOR (7). Rapamycin is widely used to suppress the immune system and prevent rejection of solid organ transplants. The best characterized immunosuppressive effects of rapamycin are based on its activities against T cells and antigen presenting cells (APCs). In mice, rapamycin causes thymic involution (16) and inhibits T cell development (17, 18), proliferation, and migration (19). When compared to effector T cells, regulatory T (Treg) cells are less sensitive to mTOR inhibition; therefore, the Treg population becomes overrepresented (20). In addition, rapamycin may directly induce Treg formation; mTOR inhibition has been shown to make T cells more sensitive to TGF-ß-induced Treg-differentiation (21). Dendritic cells (DCs) have also been described as targets of mTOR inhibition; mTOR inhibitors can suppress DC maturation (22) by interfering with antigen uptake (23). mTOR treated DCs are unable to stimulate effector T cells and may even promote the differentiation of Treg cells (23, 24). Thus, recent reports attributing immune stimulating effects to mTOR inhibition are surprising. These reports show that rapamycin can enhance vaccines targeting bacterial or virus in mouse models (9).

Renal cell carcinoma (RCC) is a classic immunoresponsive tumor. However, an effective cancer vaccine is not available for clinical use. For patients with metastatic RCC, the historical 3-year survival is less than 5% (10). Of all urologic malignancies, RCC has the highest ratio of disease-related deaths to incidence. The standard treatments for metastatic RCC include immune cytokines and small molecule targeted therapies. With targeted therapies, complete responses are rare, occurring in only 1% of patients, and patients with partial responses eventually progress and succumb to the disease (11, 12). In contrast, high dose interleukin-2 (IL2) produces complete responses and durable remissions in 5-10% of patients with metastatic RCC (10, 13, 14, 15). According to certain embodiments and as disclosed herein, the inventors show that immune-based therapies provide treatment of the advanced disease state of RCC and/or melanoma.

CD4 expressing lymphocytes include both helper T cells and regulatory T cells. T helper cells are critical to mounting an adoptive immune response. However, regulatory T cells (Tregs) inhibit the function of cytotoxic T cells and normally function to limit an immune response. Therefore, the inventors evaluated CD4 depletion as a strategy for removing Treg activity. Although only a small fraction of CD4 lymphocytes are Treg cells, CD4 depletion remains an effective approach for depleting Treg activity, and importantly, it has the potential for rapid translation to clinical use. There are humanized CD4 depleting antibodies being evaluated in clinical trials. However, there is currently no way to specifically target Foxp3 expressing cells in patients. Applicants show that the combination of mTOR inhibition and CD4 depletion has a potent antitumor immune effect, capable of inhibiting the growth of established tumors as well as hematogenous metastasis.

SUMMARY OF THE INVENTION

The invention provides methods for treating malignant neoplastic cell proliferative disorders or diseases in subjects in need thereof comprising administering an effective amount of an mTOR inhibitor and an effective amount of a CD4 lymphocyte depleting agent so as to treat malignant neoplastic cell proliferative disorders or diseases.

The invention further provides methods for inhibiting neoplastic cell proliferative disorders or diseases in subjects in need thereof comprising administering an effective amount of an mTOR inhibitor and an effective amount of a CD4 lymphocyte depleting agent so as to inhibit neoplastic cell proliferative disorders or diseases.

Also provided herein are methods for promoting prophylaxis of malignant neoplastic cell proliferative disorders or diseases in a subject in need thereof comprising administering an effective amount of an mTOR inhibitor and an effective amount of a CD4 lymphocyte depleting agent so as to promote prophylaxis of malignant neoplastic cell proliferative disorders or diseases.

The invention further provides pharmaceutical compositions comprising a therapeutically effective amount of an mTOR inhibitor and an effective amount of a CD4 lymphocyte depleting agent in a pharmaceutically acceptable carrier.

The invention also provides kits for treatment of malignant neoplastic cell proliferative disorders or diseases and/or inhibition of malignant neoplastic cell proliferative disorders or diseases and/or promoting prophylaxis of malignant neoplastic cell proliferative disorders or diseases. The kits comprise an mTOR inhibitor, a CD4 lymphocyte depleting agent and instructions for use of the composition for treatment of malignant neoplastic cell proliferative disorders or diseases and/or inhibition of malignant neoplastic cell proliferative disorders or diseases and/or promoting prophylaxis of malignant neoplastic cell proliferative disorders or diseases.

The claimed methods, compositions and kits find utility in the treatment of certain subsets of malignant neoplastic cell proliferative disorders or diseases, including but not limited to renal cell carcinomas and melanomas.

BRIEF DESCRIPTION OF THE DRAWINGS

Exemplary embodiments are illustrated in referenced figures. It is intended that the embodiments and figures disclosed herein are to be considered illustrative rather than restrictive.

(FIG. 1B) Foxp3 positive lymphocytes (Treg cells) increase in response to mTOR inhibitors.

DETAILED DESCRIPTION THE INVENTION

Figure 1A:
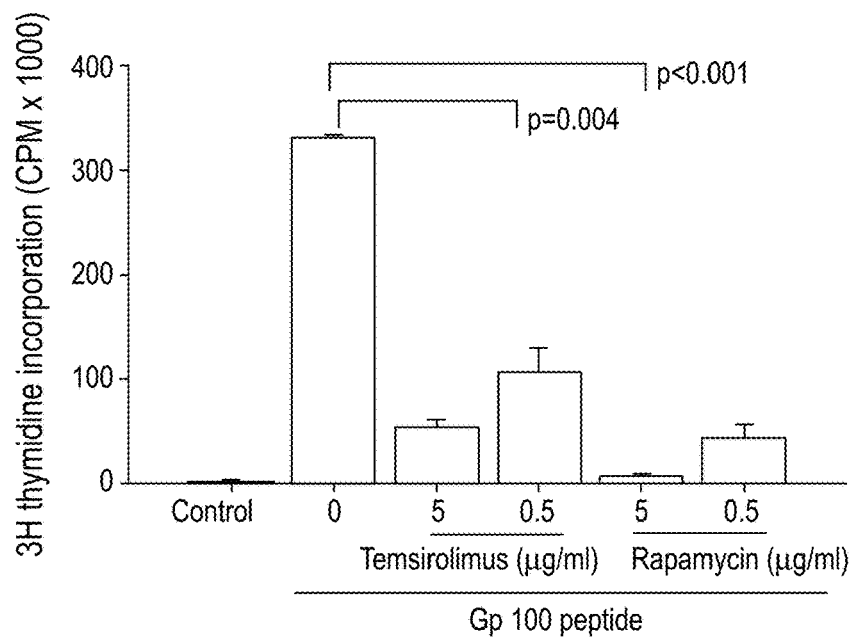
FIG. 1A-FIG. 1B shows that mTOR has immunosuppressive activity, (FIG. 1A) Tersirolimus and Rapamycin have similar activities.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Cancer" and "cancerous" refer to or describe the physiological condition in mammals that is typically characterized by unregulated cell growth. Examples of cancer include, but are not limited to, brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

"Tumor," as used herein refers to all neoplastic cell growth and proliferation, whether malignant or benign, and all pre-cancerous and cancerous cells and tissues.

"Conditions" and "disease conditions," as used herein may include, but are in no way limited to any form of malignant neoplastic cell proliferative disorders or diseases. Examples of such disorders include but are not limited to cancer. Examples of cancer include, but are not limited to, brain tumor, breast cancer, colon cancer, carcinoma, lung cancer, hepatocellular cancer, gastric cancer, pancreatic cancer, cervical cancer, ovarian cancer, liver cancer, bladder cancer, cancer of the urinary tract, thyroid cancer, renal cancer, renal cell carcinoma, melanoma, head and neck cancer, brain cancer, and prostate cancer, including but not limited to androgen-dependent prostate cancer and androgen-independent prostate cancer.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

As used herein, "CD4 lymphocytes" refer to lymphocytes which express CD4, i.e lymphocytes which are CD4+. CD4 lymphocytes may be T cells which express CD4.

The inventors have discovered that mTOR inhibition can enhance cancer vaccines by augmenting the immune response. In transplant patients, mTOR inhibitors are believed to help prevent organ rejection by increasing the activity of regulatory T cells (Treg). Therefore, as demonstrated in the Examples below, Applicants tested the effect of drugs that can counter the immune suppressing effects of mTOR inhibitors and discovered that immune stimulation can be further enhanced by these drugs. Consequently, Applicants have combined the use of mTOR inhibitors with additional drugs that deplete cells such as CD4 T cells (i.e. T cells which express CD4), thus creating a synergistic effect. According to certain embodiments, CD4 lymphocyte (i.e. lymphocytes which express CD4) depletion is used as a strategy for removing Treg activity.

The present invention provides compositions comprising one or more mTOR inhibitors and/or CD4 lymphocyte depleting agents as well as methods that employ these inventive mTOR inhibitors and/or CD4 lymphocyte depleting agents in in vivo and ex vivo applications where it is advantageous to deplete the numbers of CD4 lymphocytes and/or to reduce or eliminate the activity of mTOR or a functionally-downstream molecule.

The inventors have developed a treatment for certain subsets of cancers (e.g. renal cell carcinomas and melanomas) utilizing mTOR inhibitors and/or CD4 lymphocyte depleting agents. The inventors have determined a synergist effect of mTOR inhibitors with CD4 lymphocyte depleting agents on certain types of cancers (e.g. renal cell carcinomas and melanomas). According to particular aspects, the invention encompasses pharmaceutical compositions comprising mTOR inhibitors and/or CD4 lymphocyte depleting agents. According to further aspects, the inventors have combined the use of mTOR inhibitors with additional drugs that deplete cells such as CD4 T cells, and as such have created a synergistic effect for the treatment of malignant neoplastic cell proliferative disorders or diseases, e.g. renal cell carcinomas and melanomas. According to certain aspects, mTOR inhibitors and CD4 lymphocyte depleting agents are used in combination with other pharmaceuticals, including but not limited to cancer vaccines.

Therapeutic Methods of the Invention

The invention provides methods for treating malignant neoplastic cell proliferative disorders or diseases in subjects in need thereof. The method comprises providing a composition comprising an mTOR inhibitor and a CD4 lymphocyte depleting agent and administering a therapeutically effective amount of the composition to the subject to treat a malignant neoplastic cell proliferative disorder or disease. The composition may further comprise other pharmaceuticals, including but not limited to cancer vaccines. In one embodiment, the mTOR inhibitor is a macrolide compound including but not limited to Temsirolimus (CCI-779) or a pharmaceutical equivalent, analog, derivative or a salt thereof, Evirolimus (RAD001) or a pharmaceutical equivalent, analog, derivative or a salt thereof, and/or Rapamycin or a pharmaceutical equivalent, analog, derivative or a salt thereof. In another embodiment, an agent for depleting CD4 lymphocytes is an antibody, for example, a humanized anti-CD4 antibody such as zanolimumab. In some embodiments, malignant neoplastic cell proliferative disorder or disease is renal cell carcinoma or melanoma.

The invention further provides methods for inhibiting malignant neoplastic cell proliferative disorders or diseases in subjects in need thereof. The method comprises providing a composition comprising an mTOR inhibitor and a CD4 lymphocyte depleting agent, and administering a therapeutically effective amount of the composition to the subject to inhibit a malignant neoplastic cell proliferative disorder or disease. The composition may further comprise other pharmaceuticals, including but not limited to cancer vaccines. In one embodiment, the mTOR inhibitor is a macrolide compound including but not limited to Temsirolimus (CCI-779) or a pharmaceutical equivalent, analog, derivative or a salt thereof, Evirolimus (RAD001) or a pharmaceutical equivalent, analog, derivative or a salt thereof, and/or Rapamycin or a pharmaceutical equivalent, analog, derivative or a salt thereof. In another embodiment, an agent for depleting CD4 lymphocytes is an antibody, for example, a humanized anti-CD4 antibody such as zanolimumab. In some embodiments, malignant neoplastic cell proliferative disorder or disease is renal cell carcinoma or melanoma.

The invention further provides methods for reducing the tumor size associated malignant neoplastic cell proliferative disorders or diseases in subjects in need thereof. The method comprises providing a composition comprising an mTOR inhibitor and a CD4 lymphocyte depleting agent, and administering a therapeutically effective amount of the composition to the subject to reduce tumor size associated with malignant neoplastic cell proliferative disorder or disease. The composition may further comprise other pharmaceuticals, including but not limited to cancer vaccines. In one embodiment, the mTOR inhibitor is a macrolide compound including but not limited to Temsirolimus (CCI-779) or a pharmaceutical equivalent, analog, derivative or a salt thereof, Evirolimus (RAD001) or a pharmaceutical equivalent, analog, derivative or a salt thereof, and/or Rapamycin or a pharmaceutical equivalent, analog, derivative or a salt thereof. In another embodiment, an agent for depleting CD4 lymphocytes is an antibody, for example, a humanized anti-CD4 antibody such as zanolimumab. In some embodiments, malignant neoplastic cell proliferative disorder or disease is renal cell carcinoma or melanoma.

The invention also provides methods for promoting prophylaxis of malignant neoplastic cell proliferative disorders or diseases in subjects in need thereof. The method comprises providing a composition comprising an mTOR inhibitor and a CD4 lymphocyte depleting agent, and administering a therapeutically effective amount of the composition to the subject to promote prophylaxis of malignant neoplastic cell proliferative disorder or disease. The composition may further comprise other pharmaceuticals, including but not limited to cancer vaccines. In one embodiment, the mTOR inhibitor is a macrolide compound including but not limited to Temsirolimus (CCI-779) or a pharmaceutical equivalent, analog, derivative or a salt thereof, Evirolimus (RAD001) or a pharmaceutical equivalent, analog, derivative or a salt thereof, and/or Rapamycin or a pharmaceutical equivalent, analog, derivative or a salt thereof. In another embodiment, an agent for depleting CD4 lymphocytes is an antibody, for example, a humanized anti-CD4 antibody such as zanolimumab. In some embodiments, malignant neoplastic cell proliferative disorder or disease is renal cell carcinoma or melanoma.

In some embodiments of the invention, the mTOR inhibitor may be any one or more of a small molecule, a peptide, an antibody or a fragment thereof, a nucleic acid molecule and/or a macrolide compound. In an embodiment, the antibody specifically binds mTOR so as to inhibit mTOR. The antibody may be any one or more of a monoclonal antibody or fragment thereof, a polyclonal antibody or a fragment thereof, a chimeric antibody, a humanized antibody, a human antibody or a single chain antibody. These antibodies can be from any source, e.g., rat, dog, cat, pig, horse, mouse or human. Fragments of antibodies may be any one or more of Fab, F(ab')2, Fv fragments or fusion proteins.

In a preferred embodiment of the invention, the mTOR inhibitor is a macrolide compound. Examples of macrolide compounds that may be used with the claimed invention include but are not limited to Temsirolimus (CCI-779) or a pharmaceutical equivalent, analog, derivative or a salt thereof, Evirolimus (RAD001) or a pharmaceutical equivalent, analog, derivative or a salt thereof, and/or Rapamycin or a pharmaceutical equivalent, analog, derivative or a salt thereof.

In a further embodiment of the invention, the CD4 lymphocyte depleting agent may be any one or more of small molecule, a peptide, an antibody or a fragment thereof, a nucleic acid molecule and/or a macrolide compound. In an embodiment, the antibody specifically binds CD4 on CD4-expressing T cells such as regulatory T cells (Treg cells). The antibody may be any one or more of a monoclonal antibody or fragment thereof, a polyclonal antibody or a fragment thereof, a chimeric antibody, a humanized antibody, a human antibody or a single chain antibody. These antibodies can be from any source, e.g., rat, dog, cat, pig, horse, mouse or human. Fragments of antibodies may be any one or more of Fab, F(ab')2, Fv fragments or fusion proteins.

In a preferred embodiment of the invention, the CD4 lymphocyte depleting agent is an antibody such as a humanized anti-CD4 antibody or a fragment thereof. In the most preferred embodiment, the CD4 lymphocyte depleting antibody is zanolimumab.

In some embodiments of the invention, the mTOR inhibitor and the CD4 lymphocyte depleting agent are administered concurrently. In additional embodiments, the mTOR inhibitor and the CD4 lymphocyte depleting agent are administered sequentially. In further embodiments, the composition comprising mTOR inhibitor and the CD4 lymphocyte depleting agent are administered with food or without food. According to certain aspects, mTOR inhibitors and CD4 lymphocyte depleting agents may be used in combination with other pharmaceuticals, including but not limited to cancer vaccines.

As described above, methods for treating malignant neoplastic cell proliferative disorders or diseases, inhibiting malignant neoplastic cell proliferative disorders or diseases, reducing tumor size associated with malignant neoplastic cell proliferative disorders or diseases and promoting prophylaxis of malignant neoplastic cell proliferative disorders or diseases comprises providing and administering to the subject in need thereof, a composition comprising an mTOR inhibitor and a CD4 lymphocyte depleting agent. In one embodiment, the composition for use with the claimed methods comprises the mTOR inhibitor Temsirolimus (CCI-779) or a pharmaceutical equivalent, analog, derivative or a salt thereof and a humanized anti-CD4 antibody (such as zanolimumab) as the CD4 lymphocyte depleting agent. The mTOR inhibitor (for example Temsirolimus (CCI-779) or a pharmaceutical equivalent, analog, derivative or a salt thereof) and the CD4 lymphocyte depleting agent (for example zanolimumab) may be administered concurrently or sequentially. Additionally, the composition comprising the mTOR inhibitor Temsirolimus (CCI-779) or a pharmaceutical equivalent, analog, derivative or a salt thereof and a humanized anti-CD4 antibody (such as zanolimumab) as the CD4 lymphocyte depleting agent may further comprise a cancer vaccine.

In another embodiment, the composition for use with the claimed methods comprises the mTOR inhibitor Evirolimus (RAD001) or a pharmaceutical equivalent, analog, derivative or a salt thereof and humanized anti-CD4 antibody (such as zanolimumab) as the CD4 lymphocyte depleting agent. The mTOR inhibitor (for example Evirolimus (RAD001) or a pharmaceutical equivalent, analog, derivative or a salt thereof) and the CD4 lymphocyte depleting agent (for example zanolimumab) may be administered concurrently or sequentially. Additionally, the composition comprising the mTOR inhibitor Evirolimus (RAD001) or a pharmaceutical equivalent, analog, derivative or a salt thereof and humanized anti-CD4 antibody such as zanolimumab) as the CD4 lymphocyte depleting agent may further comprise a cancer vaccine.

In a further embodiment, the composition for use with the claimed methods comprises the mTOR inhibitor is Rapamycin or a pharmaceutical equivalent, analog, derivative or a salt thereof and humanized anti-CD4 antibody (such as zanolimumab) as the CD4 lymphocyte depleting agent. The mTOR inhibitor (for example Rapamycin or a pharmaceutical equivalent, analog, derivative or a salt thereof) and the CD4 lymphocyte depleting agent (for example zanolimumab) may be administered concurrently or sequentially. Additionally, the composition comprising the mTOR inhibitor is Rapamycin or a pharmaceutical equivalent, analog, derivative or a salt thereof and humanized anti-CD4 antibody (such as zanolimumab) as the CD4 lymphocyte depleting agent may further comprise a cancer vaccine.

The subjects treated by the present invention include mammalian subjects, including, human, monkey, ape, dog, cat, cow, horse, goat, pig, rabbit, mouse and rat.

Various methods may be utilized to administer the composition of the claimed methods, including but not limited to aerosol, nasal, oral, transmucosal, transdermal, parenteral, implantable pump, continuous infusion, topical application, capsules and/or injections.

Dosages of the Invention

In some embodiments of the invention, the effective amounts of the mTOR inhibitors in the composition for use with the claimed methods, in the pharmaceutical compositions and/or in the claimed kits may be in the range of about 0.1-0.5 mg/day, 0.5-1.0 mg/day, 1.0-1.5 mg/day, 1.5-2 mg/day, 2.0-2.5 mg/day, 2.5-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day, 95-100 mg/day, 0.75-10 mg/day or 2-10 mg/day. In some embodiments of the invention, the mTOR inhibitors are Temsirolimus (CCI-779) or a pharmaceutical equivalent, analog, derivative or a salt thereof, Evirolimus (RAD001) or a pharmaceutical equivalent, analog, derivative or a salt thereof and/or Rapamycin or a pharmaceutical equivalent, analog, derivative or a salt thereof.

In alternate embodiments, the effective amounts of the mTOR inhibitors in the composition for use with the claimed methods, in the pharmaceutical compositions and/or in the claimed kits may be in the range of about 1-5 mg/week, 5-10 mg/week, 10-15 mg/week, 15-20 mg/week, 20-25 mg/week, 25-30 mg/week, 30-35 mg/week, 35-40 mg/week, 40-45 mg/week, 45-50 mg/week, 50-55 mg/week, 55-60 mg/week, 60-65 mg/week, 65-70 mg/week, 70-75 mg/day, 75-80 mg/mg, 80-85 mg/mg, 85-90 mg/week, 90-95 mg/week or 95-100 mg/week. In some embodiments of the invention, the mTOR inhibitors are Temsirolimus (CCI-779) or a pharmaceutical equivalent, analog, derivative or a salt thereof, Evirolimus (RAD001) or a pharmaceutical equivalent, analog, derivative or a salt thereof, and/or Rapamycin or a pharmaceutical equivalent, analog, derivative or a salt thereof.

In some preferred embodiments, Temsirolimus is administered at a dose of 25 mg over 30-60 minutes per week, Evirolimus is administered at a dose of 0.75-10 mg per day and/or Rapamycin is administered at a dose of 2-10 mg per day.

In some embodiments of the invention, the effective amounts of the CD4 lymphocyte depleting agent in the composition for use with the claimed methods, in the pharmaceutical compositions and/or in the claimed kits may be in the range of about 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day or 1900-2000 mg/day. In a preferred embodiment of the invention, the CD4 lymphocyte depleting agent is a humanized anti-CD4 antibody (for example Zanolimumab dose).

In other embodiments of the invention, the effective amounts of the CD4 lymphocyte depleting agent in the composition for use with the claimed methods, in the pharmaceutical compositions and/or in the claimed kits may be in the range of about 100-200 mg/week, 200-300 mg/week, 300-400 mg/week, 400-500 mg/week, 500-600 mg/week, 600-700 mg/week, 700-800 mg/week, 800-900 mg/week, 900-1000 mg/week, 1000-1100 mg/week, 1100-1200 mg/week, 1200-1300 mg/week, 1300-1400 mg/week, 1400-1500 mg/week, 1500-1600 mg/week, 1600-1700 mg/week, 1700-1800 mg/week, 1800-1900 mg/week or 1900-2000 mg/week. In a preferred embodiment of the invention, the CD4 lymphocyte depleting agent is a humanized anti-CD4 antibody (for example Zanolimumab dose). Zanolimumab may be administered at a dose of 980 mg per week.

In an embodiment of the claimed methods of the invention, the mTOR inhibitor and the CD4 lymphocyte depleting agent may be administered simultaneously at the aforementioned dosages using the appropriate modes of administration, for instance, the modes of administration recommended by the manufacturer for each of the mTOR inhibitor and the CD4 lymphocyte depleting agent.

Alternately, the mTOR inhibitor and the CD4 lymphocyte depleting agent may be administered sequentially at the aforementioned dosages. For example, the mTOR inhibitors (for example Temsirolimus, Evirolimus or Rapamycin) may be administered, for example, daily at the aforementioned dosages and the CD4 lymphocyte depleting agent (for example a humanized anti-CD4 antibody) may be administered for example, daily, weekly, biweekly, every fortnight and/or monthly at the aforementioned dosages. Alternately, the mTOR inhibitors (for example Temsirolimus, Evirolimus or Rapamycin) may be administered, for example, daily, weekly, biweekly, every fortnight and/or monthly, at the aforementioned dosages and the CD4 lymphocyte depleting agent (for example a humanized anti-CD4 antibody) may be administered for example, daily, at the aforementioned dosages. Further, each of the mTOR inhibitor (for example Temsirolimus, Evirolimus or Rapamycin) and the CD4 lymphocyte depleting agent (for example a humanized anti-CD4 antibody) may be administered daily, weekly, biweekly, every fortnight and/or monthly, wherein the mTOR inhibitor is administered at the aforementioned dosages on a day different than the day on which the CD4 lymphocyte depleting agent is administered at the aforementioned dosages.

The cancer vaccine dose would depend on the vaccine being used. The effective dose of the cancer vaccine may be determined by one skilled in the art such as the physician) or it may be administered per the manufacturers' recommendation. In one embodiment, the first dose of the cancer vaccine is administered on day 0 and the second dose is administered on day 7. mTOR inhibitors may be administered on days 2-32, at the aforementioned dosages. Further, 2-3 weekly doses of anti-CD4 depleting agent may be administered starting on day 10, at the aforementioned dosages. For example, if a heat shock protein vaccine is used, a heat shock protein (for example, hsp110 or grp170) may be complexed with a tumor antigen (such as gp100) and subsequently administered. In an embodiment, for a melanoma vaccine, a complex of hsp110 and gp100 at 2.5 mg/g, may be administered intradermally.

Typical dosages of an effective amount of mTOR inhibitors (for example Temsirolimus (CCI-779) or a pharmaceutical equivalent, analog, derivative or a salt thereof, Evirolimus (RAD001) or a pharmaceutical equivalent, analog, derivative or a salt thereof, and/or Rapamycin or a pharmaceutical equivalent, analog, derivative or a salt thereof) or CD4 lymphocyte depleting agent can be in the ranges recommended by the manufacturer where known therapeutic compounds are used, and also as indicated to the skilled artisan by the in vitro responses or responses in animal models.

For example, the FDA approved dosage for Temsirolimus is 25 mg administered intravenously over 30-60 min every week, for Evirolimus is 0.75 mg-10 mg per day administered orally, for Rapamycin is about 2-10 mg per day administered orally and for Zanolimumab is about 980 mg per week administered intravenously. The same or similar dosing can be used in accordance with various embodiments of the present invention, or an alternate dosage may be used in connection with alternate embodiments of the invention. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

Pharmaceutical Compositions of the Invention

In various embodiments, the present invention provides pharmaceutical compositions including a pharmaceutically acceptable excipient along with a therapeutically effective amount of a mTOR inhibitor (for example Temsirolimus (CCI-779) or a pharmaceutical equivalent, analog, derivative or a salt thereof, Evirolimus (RAD001) or a pharmaceutical equivalent, analog, derivative or a salt thereof, and/or Rapamycin or a pharmaceutical equivalent, analog, derivative or a salt thereof) and a CD4 lymphocyte depleting agent (for example humanized anti-CD4 antibody such as Zanolimumab). "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. A variety of aqueous carriers may be used, e.g., water, buffered water, 0.4% saline, 0.3% glycine, and the like, and may include other proteins for enhanced stability, such as albumin, lipoprotein, globulin, etc., subjected to mild chemical modifications or the like.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral, topical or local for therapeutic treatment. Preferably, the compositions are administered orally or parenterally, i.e., intravenously, intraperitoneally, intradermally, or intramuscularly.

mTOR inhibitors and/or CD4 lymphocyte depleting agents useful in the treatment of disease in mammals will often be prepared substantially free of naturally-occurring immunoglobulins or other biological molecules. Preferred mTOR inhibitors and/or CD4 lymphocyte depleting agents will also exhibit minimal toxicity when administered to a mammal.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers e.g., 1-20% maltose, etc.).

According to certain aspects, mTOR inhibitors may include, but are not limited to, rapamycin, Temsirolimus, (CCI-779) and Evirolimus (RAD001). According to certain aspects, CD4 lymphocyte depleting agents include, but are not limited to, humanized anti-CD4 antibodies such as zanolimumab.

Kits of the Invention

The present invention is also directed to articles of manufacture and kits containing mTOR inhibitors and CD4 lymphocyte depleting agents for therapeutic methods described above. mTOR inhibitors include but are not limited to mTOR inhibitor (for example Temsirolimus (CCI-779) or a pharmaceutical equivalent, analog, derivative or a salt thereof, Evirolimus (RAD001) or a pharmaceutical equivalent, analog, derivative or a salt thereof, and/or Rapamycin or a pharmaceutical equivalent, analog, derivative or a salt thereof). CD4 lymphocyte depleting agents include but are not limited to humanized anti-CD4 antibody, such as Zanolimumab.

In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to affect a desired outcome. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are offered for illustrative purposes only, and are not intended to limit the scope of the present invention in any way.

Example 1 mTOR has Immunosuppressive Activity

As has been well established, mTOR inhibitors have immune suppressing activity. For the [3H] thymidine incorporation assay, lymph nodes were harvested from naïve C57 BL/6 or Pmel-1 mouse, $3 \times 10^5$ cells/well were cultured in 96-well plates and stimulated, with or without mTOR inhibitors, for 72 hours. C57 BL/6 lymphocytes were stimulated with anti-CD3 and anti-CD28 mAb, and Pmel-1 lymphocytes were stimulated with gp1.00 peptide. DNA synthesis was determined by incubation for 16 h with 1 µCi [3H] thymidine (Amersham Biosciences, Piscataway, N.J., USA). As shown in FIG. 1A the two mTOR inhibitors, namely temsirolimus and rapamycin have nearly identical activities.

Figure 1B:
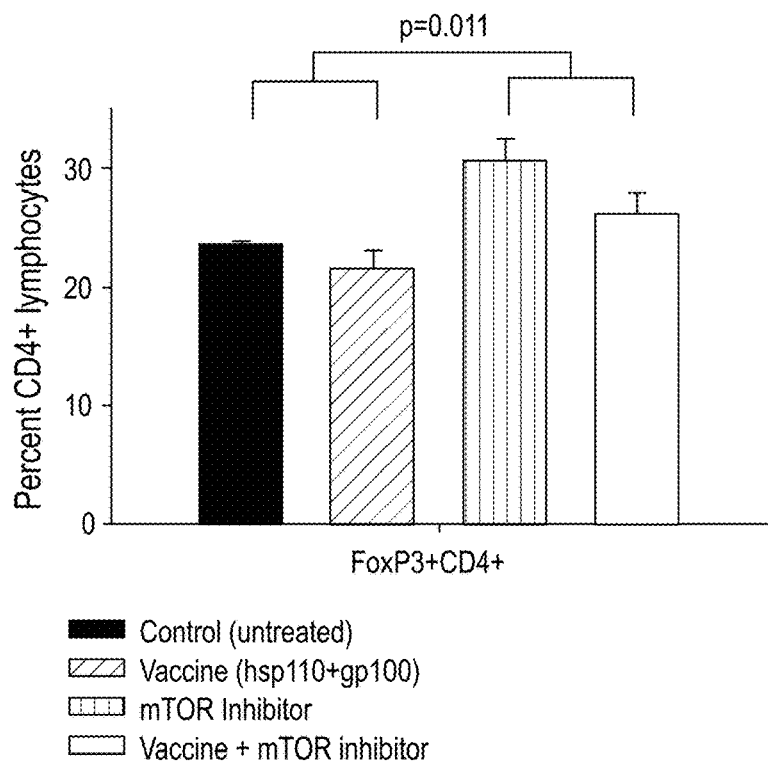

Further, in vivo effect of temsirolimus on CD4+FoxP3+ lymphocytes was assessed. B6 mice (5 mice per group) were treated daily with temsirolimus for 24 days, 2 doses of vaccine (complex of hsp110 and gp100), or both. FoxP3 staining was quantified with flow cytometry while gating on CD4. As shown in FIG. 1B, Foxp3 positive lymphocytes (regulatory T cells) are increased by mTOR inhibition. Data show mean and standard error of the mean (s.e.m). Representative results are shown from at least 2 independent experiments. Based on these data, inventors adapted the strategy of CD4 depletion as a strategy for removing these regulatory T cells (Tregs).

Example 2

The Combination of CD4 Depletion and Termsirolimus was an Effective Treatment for B16 Tumors In this Example, the inventors tested their combinational therapy strategy, wherein mTOR inhibitors were combined with a strategy to deplete regulatory T cells (Treg, cells) in mouse tumor model of B16 melanoma. Mice with established B16 melanoma tumors, which are very immunoresistent tumors, were treated with the combination of temsirolimus and CD4 depleting antibodies.

Figure 2:
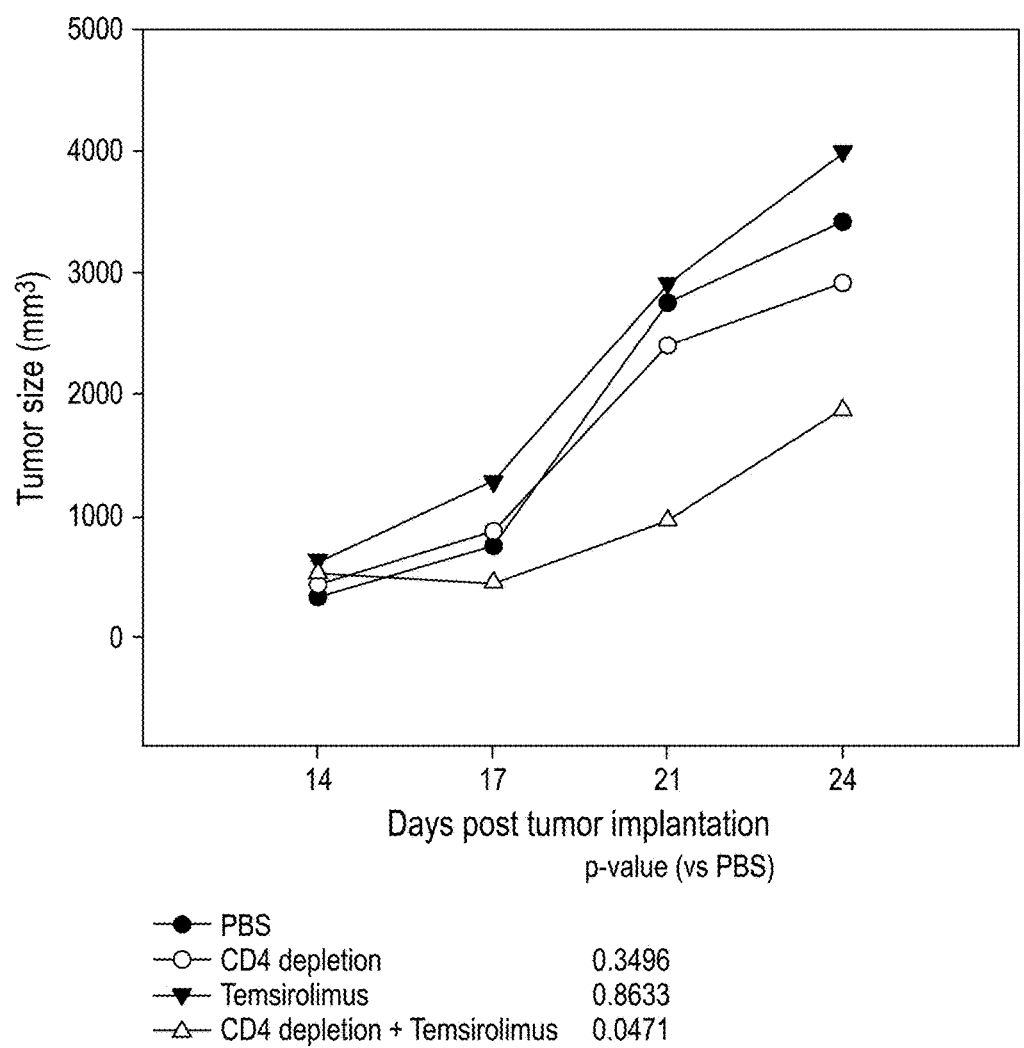
FIG. 2 shows that, in accordance with an embodiment of the invention, the combination of CD4 depletion and termsirolimus was an effective treatment for B16 tumors.

Ten days after subcutaneous implantation of tumor cells B6 mice were treated with PBS (control), temsirolimus, CD4 depleting antibody (intraperitoneal injection of 200 μg of GK1.5 mAb, administered every other day for 6 days, starting at day 4), or both (temsirolimus and CD4 depleting antibody). The tumor growth was monitored. Each line in FIG. 2 represents mean tumor growth and standard error of the mean (s.e.m), in five animals. P-values are for repeated measures ANOVA. As shown in FIG. 2, this combination was effective in slowing the growth of B16 tumors.

Example 3

Combination of CD4 Lymphocyte Depletion and Temsirolimus was an Effective Treatment for RENCA Tumors In this Example, the inventors tested their combinational therapy strategy, wherein mTOR inhibitors were combined with a strategy to deplete regulatory T cells (Treg cells) in mouse tumor model of RENCA tumors. RENCA is a murine renal cancer cell and model.

Figure 3:
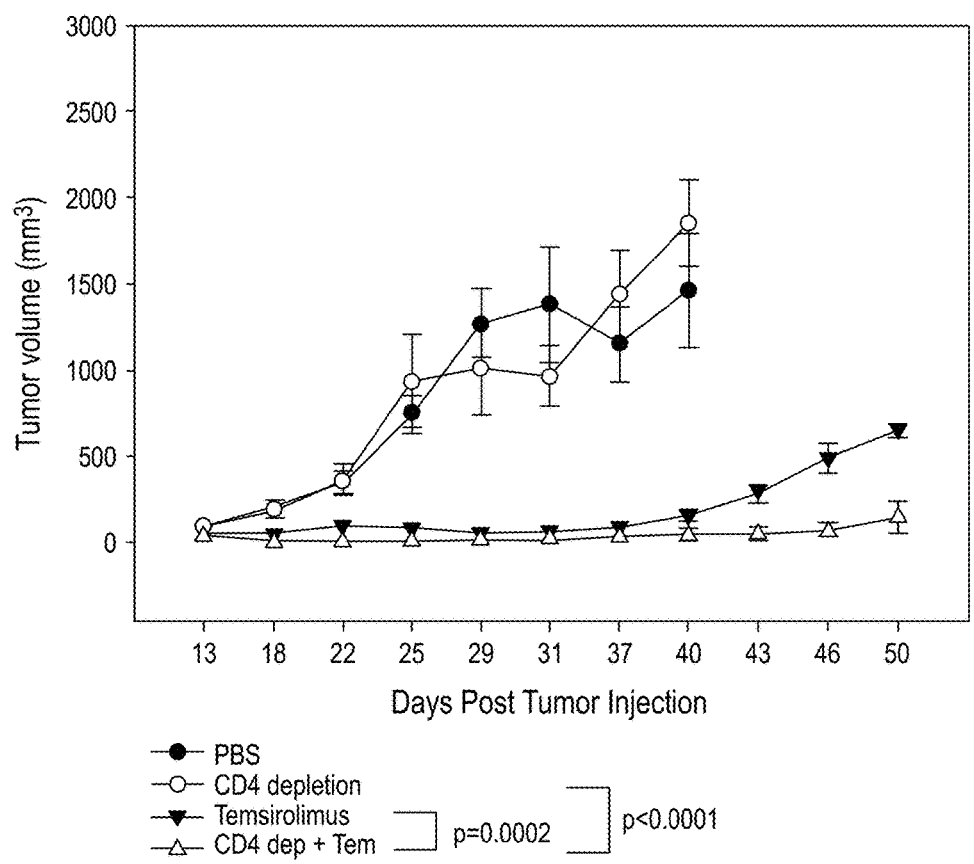
FIG. 3 shows that, in accordance with an embodiment of the invention, the combination of CD4 depletion and termsirolimus was an effective treatment for RENCA tumors.

Ten days after subcutaneous implantation of RENCA tumor cells, Balb/c mice were treated with PBS (control), temsirolimus, CD4 depleting antibody (intraperitoneal injection of 200 μg of GK1.5 mAb, administered every other day for 6 days, starting at day 4), or both (temsirolimus and CD4 depleting antibody). The tumor growth was monitored. Each line in FIG. 3 represents mean tumor growth and standard error of the mean (s.e.m) in five animals. P-values are for repeated measures ANOVA. As shown in FIG. 3, this combination was effective in curing three of five mice with established tumors, even though a specific tumor vaccine was not included.

Example 4

Combinational Therapy Strategy Produces Antitumor Immune Memory

Figure 4:
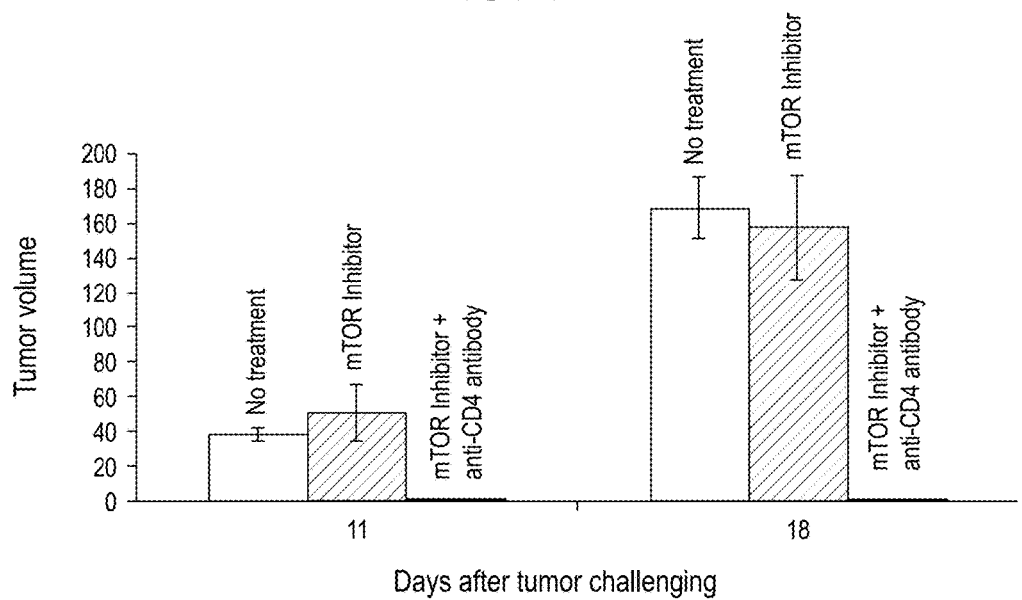
FIG. 4 shows that, in accordance with an embodiment of the invention, combinational therapy produces antitumor immune memory.

Ten days after subcutaneous implantation of $2 \times 10^5$ tumor cells, Balb/c mice were treated with temsirolimus (30 ug/mouse daily on days 14 to 34, intraperitoneally) or temsirolimus plus CD4 depleting antibody (intraperitoneal injection of 200 μg of GK1.5 mAb, administered at day 6 and 10). Mice were re-challenged with $2 \times 10^5$ RENCA tumor cells on day 47. Naïve mouse group was also challenged with RENCA and served as a control. Tumor size was measured 11 and 18 days after the re-challenge. The tumor grew at the same rate in untreated mice and mice treated with temsirolimus alone. However, in the mice treated with both temsirolimus and CD4 depletion the tumor did not grow (FIG. 4). Since the mice were not being actively treated at the time of tumor re-challenge, direct antitumor effects of the therapy cannot account for the effects on tumor growth. These data suggest that indirect immune effects persist after treatment and account for the observed inhibition of tumor growth.

Example 5

Figure 5:
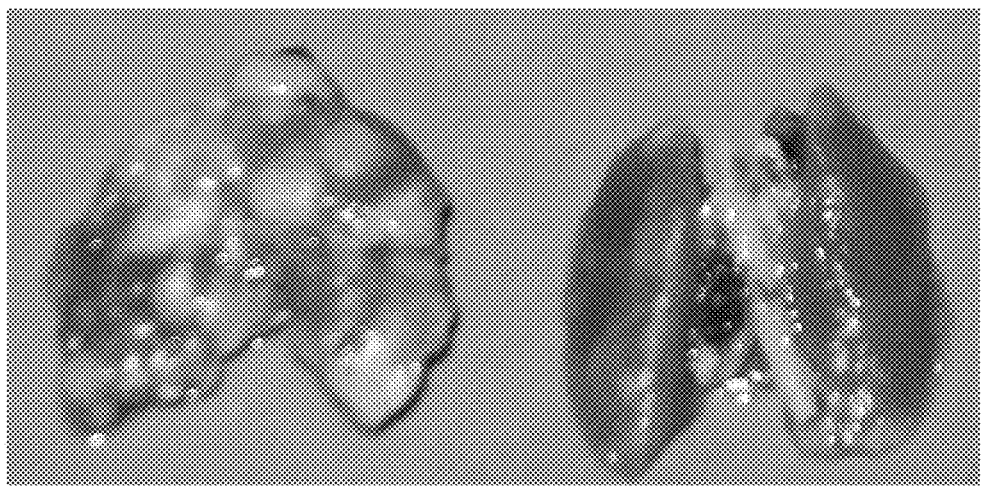
FIG. 5 shows that, in accordance with an embodiment of the invention, combinational therapy produces antitumor immune memory effect that inhibits tumor growth in a mouse model of metastatic disease.

Combinational Therapy Produces Antitumor Immune Memory Effect that Inhibits Tumor Growth in a Mouse Model of Metastatic Disease RENCA tumor cells ($2 \times 10^5$ cells) were injected subcutaneously into the flank of Balb/c mice, CD4 depleting antibody was administered twice on days 6 and 10, and temsirolimus (15 ug/mouse) was administered daily from days 14 to day 34. On day 91, mice were rechallenged with RENCA tumor cells ($2 \times 10^5$) injected intravenously. The mouse lungs were examined for tumor growth 30 days after the rechallenge (FIG. 5). The combinational therapy inhibited the establishment and growth of RENCA tumors in the lung.

Example 6

Combinational Therapy Activates Cytotoxic T Lymphocytes

Figure 6:
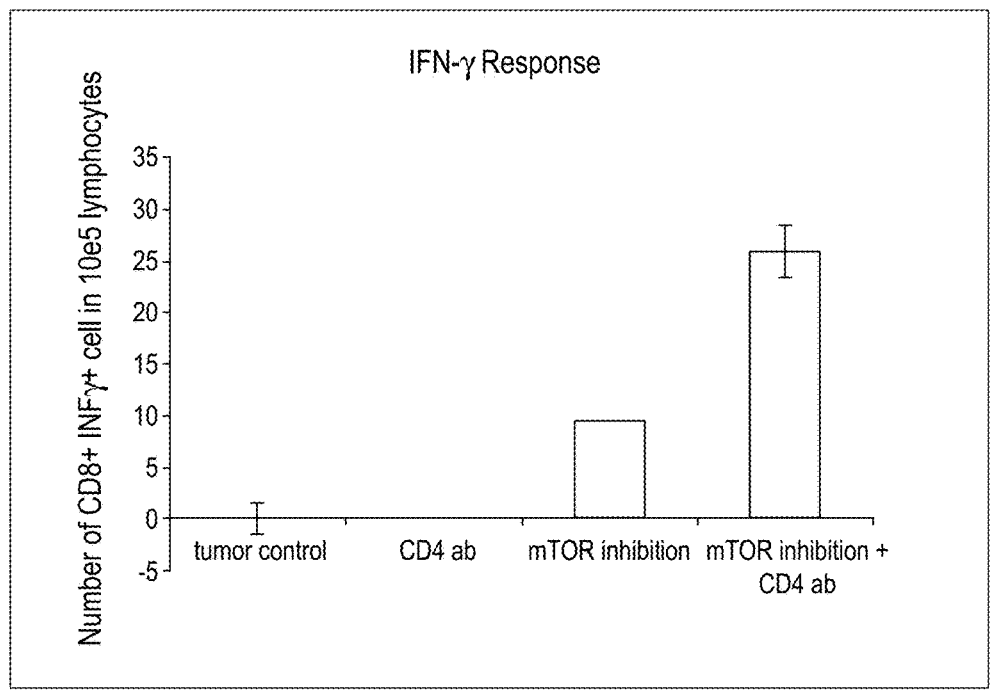
FIG. 6 shows that, in accordance with an embodiment of the invention, combinational therapy activates T lymphocytes as measured by the IFN-gamma (IFN-γ) response.

RENCA tumor cells expressing CA9 were injected subcutaneously into the flank of Balb/c mice. Mice were treated as described in Example 3. Lymph nodes were harvested 35 days after tumor implantation. Lymphocytes were activated in vitro with CA9 protein (10 μg/ml) at 37° C. for 48 h, then washed and intracellular stained with IFN-γ. Flow cytometry was performed using the FACScan to analyze IFN-gamma (IFNγ, IFN-γ) expression, while gating on CD8. As shown in FIG. 6, combination therapy activates cytotoxic T lymphocytes as measured by the IFN-gamma response.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

REFERENCES

1. Brown E J, Albers M W, Shin T B, Ichikawa K, Keith C T, Lane W S, Schreiber S L (June 1994). "A mammalian 1. protein targeted by G1-arresting rapamycin-receptor complex". Nature 369 (6483): 756-758.
2. Moore P A, Rosen C A, Carter K C (April 1996), "Assignment of the human FKBP12-rapamycin-associated protein (FRAP) gene to chromosome 1p36 by fluorescence in situ hybridization". Genomics 33 (2): 331-332.
3. Hay N, Sonenberg N (2004). "Upstream and downstream of mTOR". Genes Dev 18 (16): 1926-45.
4. Beevers C, Li F, Liu L, Huang S (2006). "Curcumin inhibits the mammalian target of rapamycin-mediated signaling pathways in cancer cells". Int J Cancer 119 (4): 757-64.
5. Tokunaga C, Yoshino K, Yonezawa K (2004). "mTOR integrates amino acid- and energy-sensing pathways". Biochem Biophys Res Commun 313 (2): 443-6.
6. Huang S, Houghton P (2001). "Mechanisms of resistance to rapamycins". Drug Resist Updat 4 (6): 378-91.
7. Huang S, Bjornsti M, Houghton P (2003). "Rapamycins: mechanism of action and cellular resistance". Cancer Biol Ther 2 (3): 222-32
8. Jagannath C. Lindsey D R, Dhandayuthapani S, Xu Y, Hunter R L, Jr., Elissa N T. Autophagy enhances the efficacy of BCG vaccine by increasing peptide presentation in mouse dendritic cells. Nat Med 2009; 15:267-76.
9. Araki K. Turner A P, Shaffer V O, Gangappa S, Keller S A, Bachmann M F et al. mTOR regulates memory CD8 T-cell differentiation. Nature 2009; 260: 108-12.
10. Figlin R A, Renal cell carcinoma; management of advanced disease, J Urol 1999; 161:381-6; discussion 6-7.
11. Motzer R J, Rini B I, Bukowski R M, Curti B D, George D J, Hudes G R et al. Sunitinib in patients with metastatic renal cell carcinoma. Jama 2006; 295:2516-24.
12. Hutson T E, Figlin R A. Novel therapeutics for metastatic renal cell carcinoma. Cancer 2009; 115:2361-7.
13. Bukowski R M. Cytokine combination: therapeutic use in patients with advanced renal cell carcinoma. Semin Oncol 2000; 27:204-12.
14. Fisher R J, Rosenberg S A, Sznol M, Parkinson D R, Fyfe G. High-dose aldesleukin in renal cell carcinoma: long-term survival update. Cancer J Sci Am 1997; 3 Suppl 1:S70-02.
15. Rethinking therapeutic cancer vaccines. Nat Rev Drug Discov. 2009; 8(9):685-6.
16. Luo H, Duguid W, Chen H, Maheu M, Wu J. The effect of rapamycin on T cell development in mice, Eur J Immunol. 1994; 24(3):692-701.
17. Mondino A, Mueller D L. mTOR at the crossroads of T cell proliferation and tolerance. Semin Immunol. 2007; 19(3):162-72. PMCID: 1995654.
18. Song J. Salek-Ardakani S, So T, Croft M. The kinases aurora B and mTOR regulate the G1-S cell cycle progression of T lymphocytes. Nat Immunol. 2007; 8(1):64-73.
19. inclair L V, Finlay D, Feijoo C, Cornish G H, Gray A, Ager A, Okkenhaug K, Hagenbeek T J, Spits H, Cantrell D A. Phosphatidylinositol-3-OH kinase and nutrient-sensing mTOR pathways control T lymphocyte trafficking. Nat Immunol. 2008; 9(5):513-21.
20. Battaglia M, Stabilini A, Migliavacca B, Horejs-Hoeck J, Kaupper T, Roncarolo M G. Rapamycin promotes expansion of functional CD4+CD25+FOXP3+ regulatory T cells of both healthy subjects and type 1 diabetic patients. J Immunol. 2006; 177(12):8338-47.
21. Delgoffe G M, Kole T P, Zheng Y, Zarek P E, Matthews K L, Xiao B, Worley P F, Kozma S C, Powell J D. The mTOR kinase differentially regulates effector and regulatory T cell lineage commitment. Immunity. 2009; 30(6): 832-44. PMCID: 2768135.
22. Hackstein H, Taner T, Zahorchak A F, Morelli A E, Logar A J, Gessner A, Thomson A W. Rapamycin inhibits IL-4-induced dendritic cell maturation in vitro and dendritic cell mobilization and function in vivo. Blood. 2003; 101(11):4457-63.
23. Monti P, Mercalli A, Leone B E, Valerio D C, Allavena P, Piemonti L. Rapamycin impairs antigen uptake of human dendritic cells. Transplantation. 2003; 75(1):137-45.
24. Tumquist H R, Raimondi G, Zahorchak A F, Fischer R T, Wang Z, Thomson A W. Rapamycin-conditioned dendritic cells are poor stimulators of allogeneic CD4+ T cells, but enrich for antigen-specific Foxp3+ T regulatory cells and promote organ transplant tolerance. J Immunol. 2007; 178(11):7018-31.

What is claimed is:

1. A method of treating or inhibiting metastasis of a carcinoma or melanoma in a subject in need thereof, wherein the subject has been diagnosed with the carcinoma or melanoma, consisting essentially of:
   administering a therapeutically effective amount of an mTOR inhibitor to the subject, wherein the mTOR inhibitor is selected from the group consisting of (i) temsirolimus (CCI-779) or a pharmaceutical equivalent, analog, derivative or a salt thereof, (ii) Everolimus (RAD001) or a pharmaceutical equivalent, analog, derivative or a salt thereof, and (iii) Rapamycin or a pharmaceutical equivalent, analog, derivative or a salt thereof; and
   administering a therapeutically effective amount of an anti-CD4 antibody or an antigen-binding fragment thereof to the subject, so as to treat or inhibit metastasis of the carcinoma or melanoma.

2. A method of obtaining beneficial results in a subject with a carcinoma or melanoma, consisting essentially of:
   administering a therapeutically effective amount of an mTOR inhibitor to the subject, wherein the mTOR inhibitor is selected from the group consisting of (i) temsirolimus (CCI-779) or a pharmaceutical equivalent, analog, derivative or a salt thereof, (ii) Everolimus (RAD001) or a pharmaceutical equivalent, analog, derivative or a salt thereof, and (iii) Rapamycin or a pharmaceutical equivalent, analog, derivative or a salt thereof; and
   administering a therapeutically effective amount of an anti-CD4 antibody or an antigen-binding fragment thereof to the subject, so as to obtain beneficial results in the subject.

3. A method of slowing down a carcinoma or melanoma, lessening the severity of a carcinoma or melanoma or alleviating the severity of a carcinoma or melanoma in a subject, consisting essentially of:
   administering a therapeutically effective amount of an mTOR inhibitor to the subject, wherein the mTOR inhibitor is selected from the group consisting of (i) temsirolimus (CCI-779) or a pharmaceutical equivalent, analog, derivative or a salt thereof, (ii) Everolimus (RAD001) or a pharmaceutical equivalent, analog, derivative or a salt thereof, and (iii) Rapamycin or a pharmaceutical equivalent, analog, derivative or a salt thereof; and
   administering a therapeutically effective amount of an anti-CD4 antibody or an antigen-binding fragment thereof to the subject, so as to lessen or alleviate the severity of the carcinoma or melanoma.

4. A method of reducing the tumor size of a carcinoma or melanoma in a subject, consisting essentially of:
  administering a therapeutically effective amount of an mTOR inhibitor to the subject, wherein the mTOR inhibitor is selected from the group consisting of (i) temsirolimus (CCI-779) or a pharmaceutical equivalent, analog, derivative or a salt thereof, (ii) Everolimus (RAD001) or a pharmaceutical equivalent, analog, derivative or a salt thereof, and (iii) Rapamycin or a pharmaceutical equivalent, analog, derivative or a salt thereof; and
  administering a therapeutically effective amount of an anti-CD4 antibody or an antigen-binding fragment thereof to the subject, so as to reduce the tumor size of the carcinoma or melanoma.

5. The method of claim 1, 2, 3 or 4, wherein the mTOR inhibitor and the anti-CD4 antibody or an antigen-binding fragment thereof are administered concurrently.

6. The method of claim 1, 2, 3 or 4, wherein the mTOR inhibitor and the anti-CD4 antibody or an antigen-binding fragment thereof are administered sequentially.

7. The method of claim 1, 2, 3 or 4, wherein the anti-CD4 antibody is a monoclonal antibody or an antigen-binding fragment thereof, a polyclonal antibody or an antigen-binding fragment thereof, a chimeric antibody, a humanized antibody, a human antibody or a single chain antibody.

8. The method of claim 1, 2, 3 or 4, wherein the anti-CD4 antibody is a humanized anti-CD4 antibody.

9. The method of claim 1, 2, 3 or 4, wherein the anti-CD4 antibody is zanolimumab.

10. The method of claim 1, 2, 3 or 4, wherein the carcinoma is a renal cell carcinoma.

11. The method of claim 1, 2, 3 or 4, wherein the effective amount of the mTOR inhibitor is 0.1-0.5 mg/day, 0.5-1.0 mg/day, 1.0-1.5 mg/day, 1.5-2 mg/day, 2.0-2.5 mg/day, 2.5-5 mg/day, 5-10 mg/day, 10-15 mg/day, 15-20 mg/day, 20-25 mg/day, 25-30 mg/day, 30-35 mg/day, 35-40 mg/day, 40-45 mg/day, 45-50 mg/day, 50-55 mg/day, 55-60 mg/day, 60-65 mg/day, 65-70 mg/day, 70-75 mg/day, 75-80 mg/day, 80-85 mg/day, 85-90 mg/day, 90-95 mg/day or 95-100 mg/day.

12. The method of claim 1, 2, 3 or 4, wherein the effective amount of the anti-CD4 antibody or an antigen-binding fragment thereof is 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day or 1900-2000 mg/day.

13. The method of claim 1, 2, 3 or 4, wherein the mTOR inhibitor and/or the anti-CD4 antibody or an antigen-binding fragment thereof is administered intravenously, intramuscularly, intraperitoneally, orally or via inhalation.

* * * * *